(12) United States Patent
Sugimoto et al.

(10) Patent No.: US 6,231,503 B1
(45) Date of Patent: May 15, 2001

(54) ENDOSCOPIC LIGHT SOURCE APPARATUS (75) Inventors: Hideo Sugimoto; Kenichi Iriyama, both of Tokyo (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/330,021

(22) Filed: Jun. 11, 1999

(30) Foreign Application Priority Data

Jun. 11, 1998 (JP) .................................................. 10-163292

(51) Int. Cl.[7] ...................................................... A61B 1/06
(52) U.S. Cl. .......................... 600/178; 600/181; 362/583; 362/574
(58) Field of Search ..................................... 600/178, 181, 600/132; 362/583, 574

(56) References Cited

U.S. PATENT DOCUMENTS 4,862,258 * 8/1989 Kidawara et al. ..................... 358/98
4,951,133 * 8/1990 Onoda ..................................... 358/98
5,823,943 * 10/1998 Tomioka et al. ...................... 60/178
5,876,327 * 3/1999 Tsuyuki et al. ....................... 600/112

* cited by examiner

Primary Examiner—Lee Cohen
Assistant Examiner—Jocelyn Ram
(74) Attorney, Agent, or Firm—Greenblum & Bernstein, P.L.C.

(57) ABSTRACT

The endoscopic light source apparatus has an illuminating light converging mechanism (20) in which a lightguide connector (3) to be connected displaces a condenser lens (22) in a direction parallel to the optical axis of illuminating light so that irrespective of the length of the lightguide connector (3), the illuminating light entrance end face (4a) of the lightguide connector (3) is located near the position in which the rays of illuminating light converge, and a filter inserting and retracting mechanism (30) which moves in operative association with the illuminating light converging mechanism (20) such that a light attenuating filter (31) is inserted into or retracted from the rays of illuminating light depending upon the length of the lightguide connector (3).

9 Claims, 6 Drawing Sheets

ENDOSCOPIC LIGHT SOURCE APPARATUS

BACKGROUND OF THE INVENTION

The present invention relates to an endoscopic light source apparatus for supplying illuminating light to an endoscope.

Endoscopic light source apparatus are generally of such a type that rays of illuminating light emitted from a light source, such as a built-in lamp are allowed to converge with a condenser lens and the illuminating light entrance end face of an endoscope's lightguide connector is connected near the position of their convergence.

Such endoscopic light source apparatus are useful in combination with various types of endoscopes to constitute an endoscopic system. That is, various types or kinds of endoscopes are preliminarily prepared depending on various intended uses, and selectively connected for use with a single unit of light source apparatus. To this end, the lightguide connector to be connected to the light source apparatus has the same shape and size in spite of the use of different models of endoscope. Therefore, any one of endoscopes belonging to an endoscopic system can be connected to a light source apparatus belonging to the same endoscopic system.

If the endoscopic system itself is renewed for various reasons such as making substantial modification, it is often necessary to change the size and shape of the joint between the endoscope's lightguide connector and the light source apparatus.

In renewal of the endoscopic system, there is no big problem with the light source apparatus since only one unit need be replaced. However, substituting an entirely new set of endoscopes often means an excessive economic burden on the user. To deal with this problem, the light source apparatus in a new system is generally adapted to be of such a compatible type that not only the endoscopes for the new system but also those for the old system can be connected.

In this connection, the endoscope belonging to the old system generally has a relatively long insertion section on the lightguide as a support to the light source apparatus in order to secure the positional accuracy of the illuminating light entrance end face of the endoscope's lightguide connector relative to the convergence position of the rays of illuminating light emitted from the light source lamp. In contrast, the endoscope belonging to the new system does not require such long insertion section on the lightguide since the positional accuracy can be secured by other means or mechanisms, and therefore the design trend is making the insertion section of the lightguide shorter from the viewpoint of space-saving.

However, some types of the endoscopes belonging to the new endoscopic system require the light source apparatus belonging to the new endoscopic system to have a light attenuating filter in the form of a metal screen between a lamp, i.e. the light source, and the illuminating light entrance end face of a lightguide connector in order to ensure that heat rays included in the illuminating light radiated from the lamp will not raise the temperature of the lightguide connector portion to an unduly high level that may cause a burn to the operator. An endoscope that has a relatively long insertion section on a lightguide similarly to the endoscope belonging to the old endoscopic system (and thus a distance between the light source lamp and the illuminating light entrance end face of the lightguide connector is inevitably short), an endoscope that uses a thermally weak material, such as plastic fiber (which is advantageous in view of cost reduction and which would be put into practice near future), as the lightguide, etc. are included in those types of the endoscopes.

A problem with a light source apparatus of this design is that if it is connected to an endoscope in a system that does not have to use such a light attenuating filter, the efficiency of illumination is insufficient to produce an adequate brightness of illuminating light whereas if the combination is reversed, the temperature of the lightguide connector portion is raised to an unduly high level that may potentially cause a burn to the operator.

SUMMARY OF THE INVENTION

The present invention has been accomplished under these circumstances, and has as an object providing an endoscopic light source apparatus to which either an endoscope in a system that requires a light attenuating filter in the optical path of illuminating light or an endoscope in a system that does not need such a light attenuating filter can be connected for use without any problem.

To achieve the stated object, the present invention provides such an arrangement that the light attenuating filter is inserted into or retracted from the optical path of illuminating light depending upon the length of the lightguide connector to be connected to the light source apparatus. The present invention further provides such an arrangement that, irrespective of the length of the lightguide connector, the illuminating light entrance end face of the lightguide connector is always located near the position in which the rays of illuminating light converge. Accordingly, various types of endoscopes can be used in the appropriate way irrespective of whether they are intended for a system that requires a light attenuating filter in the optical path of illuminating light or for a system that needs no such filters.

The present invention provides, as an embodiment, an endoscopic light source apparatus in which the illuminating light entrance end face of an endoscope's lightguide connector is connected near a converging position in which the rays of illuminating light emitted from a light source are allowed to converge with a condenser lens, characterized by having an illuminating light converging mechanism in which said lightguide connector to be connected displaces said condenser lens in a direction parallel to the optical axis of the illuminating light so that irrespective of the length of said lightguide connector, the illuminating light entrance end face of said lightguide connector is located near the converging position of said rays of illuminating light, and a filter inserting and retracting mechanism which moves in operative association with said illuminating light converging mechanism such that a light attenuating filter is inserted into or retracted from said rays of illuminating light depending upon the length of said lightguide connector.

If desired, said filter inserting and retracting mechanism may be adapted to be driven by the operation of said illuminating light converging mechanism. Alternatively, it may be adapted to allow said light attenuating filter to be inserted or retracted in a direction normal to said optical axis of the illuminating light.

In another modification, said light attenuating filter may be inserted into said rays of illuminating light when said lightguide connector is long enough but it is not inserted into said rays of illuminating light when said lightguide connector is short. Alternatively, said light attenuating filter may be inserted into said rays of illuminating light when said lightguide connector is short but it is not inserted into said rays of illuminating light when said lightguide connector is long enough.

In a preferred embodiment, the rays of illuminating light emitted from said light source may consist of rays of both parallel light and diffusing light.

The present disclosure relates to the subject matter contained in Japanese patent application No. Hei. 10-163292 (filed on Jun. 11, 1998), which is expressly incorporated herein by reference in its entirety.

DETAILED DESCRIPTION OF THE PREFERRED EMBODIMENT

A preferred embodiment of the invention is hereunder described with reference to the accompanying drawings.

Figure 5:
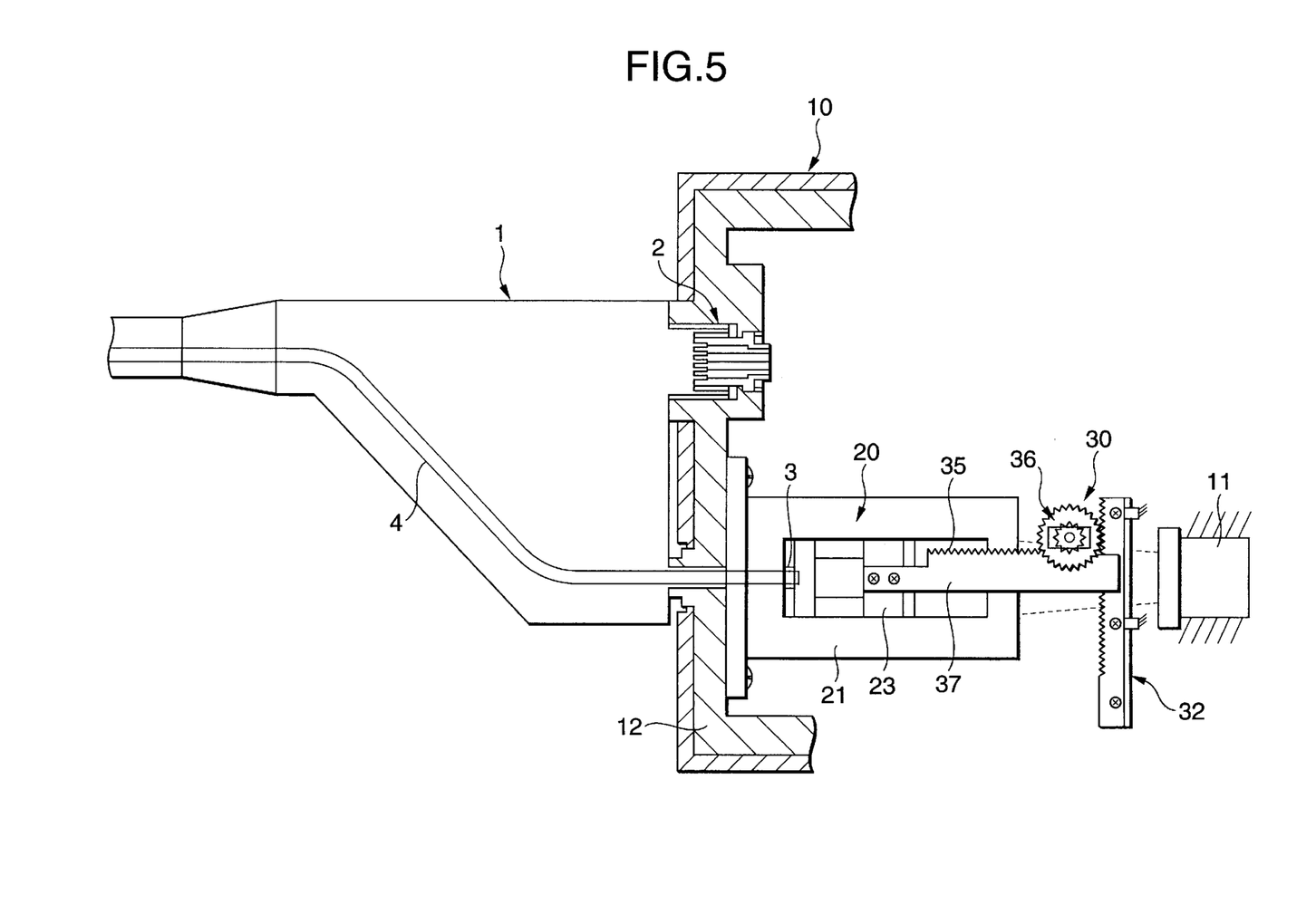
FIG. 5 is a diagram showing in partial longitudinal section how the endoscope's connector portion in the embodiment of the invention is connected to a light source apparatus.

FIG. 5 shows the joint between a connector portion 1 of an endoscope and a light source apparatus 10.

The connector portion 1 can be attached to or detached from the light source apparatus 10. If attached to the light source apparatus 10, the connector portion 1 permits simultaneous connection with a connector 2 for transmission of electrical signals and a lightguide connector 3.

If an electronic endoscope is connected, picture signals or the like that are captured with a solid-state imaging device are transmitted through the connector 2. If an optical endoscope is connected, signals for shooting with automatic exposure and the like are transmitted through the connector 2.

The lightguide connector 3 is of such a design that the rays of illuminating light radiated from a lamp 11, i.e. the light source that is fixed to the frame 12 of the light source apparatus 10, are entered into an endoscope's illuminating lightguide fiber bundle 4.

The lightguide connector 3 is formed as a rod that projects from an end of the connector portion 1 such that its tip is inserted into an illuminating light converging mechanism 20 provided within the light source apparatus 10. A filter inserting and retracting mechanism 30 is provided between the light source lamp 11 and the illuminating light converging mechanism 20 to allow a light attenuating filter to be inserted into or retracted from the rays of illuminating light.

Figure 1:
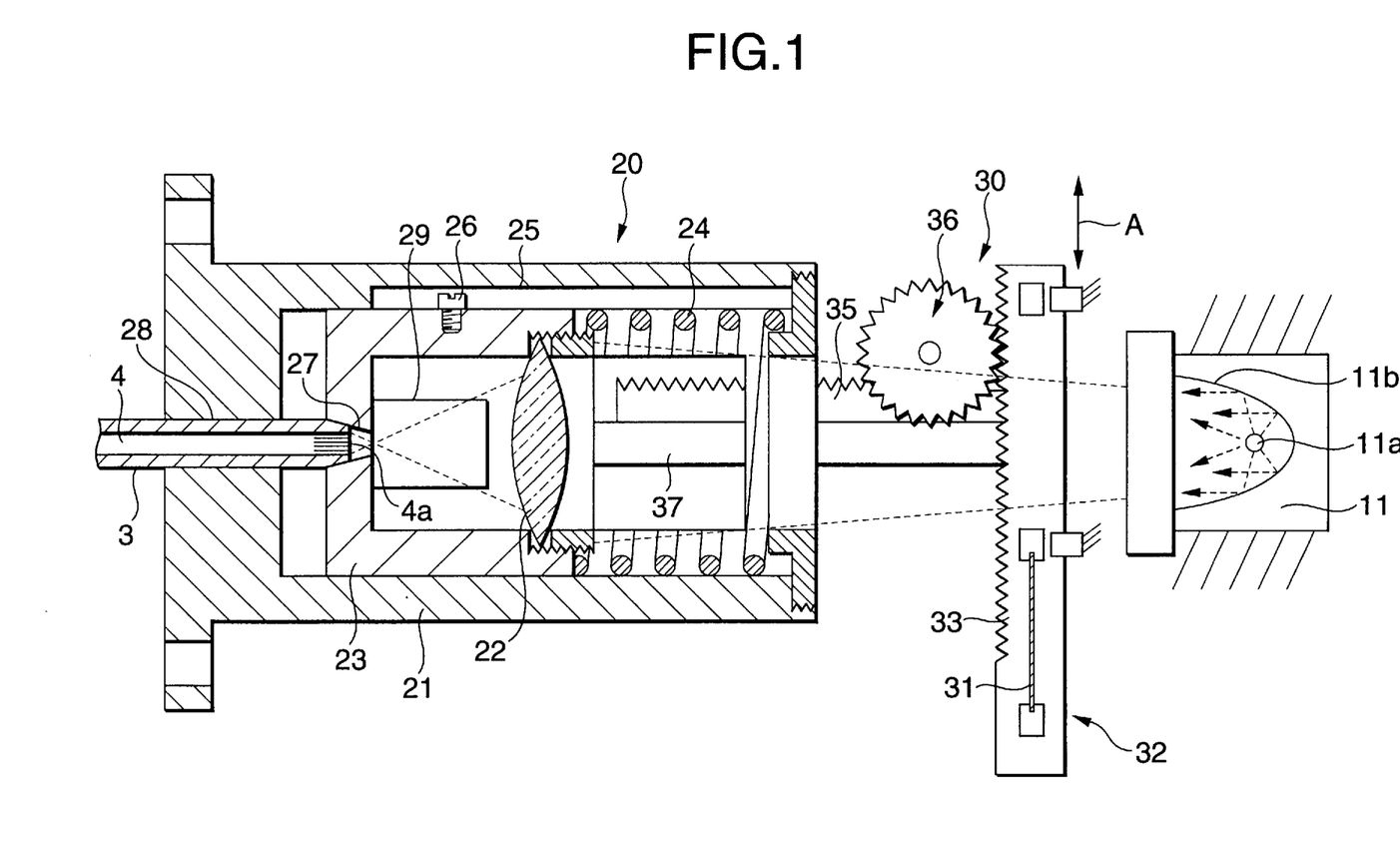
FIG. 1 is a longitudinal section of an embodiment of the invention in which a short lightguide connector is connected to a light source apparatus.

FIG. 1 shows, in an enlarged manner, the mechanism between the lightguide connector 3 connected to the light source apparatus 10 and the light source lamp 11. The lightguide connector 3 which is shown to be connected to the light source apparatus 10 in FIG. 1 is of a short type that is used in a new endoscopic system.

The light source lamp 11 is made up of a light emitter 11a and a parabolic mirror 11b in the form of a "cold mirror" which reflects visible light but absorbs heat rays. The light reflected from the parabolic mirror 11b is substantially collimated and radiated forward.

It should however be noted that the rays of light directly radiated forward from the light emitter 11a are those of diffusing light including heat rays; hence, taken as a whole, the rays of illuminating light radiated from the lamp 11 consist of rays of both parallel light and diffusing light. In a case where the lightguide connector 4 is short, a distance between the lightguide end face 4a of the lightguide fiber bundle 4 and the light source lamp 11 is long, so that a ratio of quantity of the diffusing light relative to the entire quantity of the converged illuminating light is small in comparison with a case where the light guide connector 4 is long, and therefore the light attenuating filter can be dispensed with.

The illuminating light converging mechanism 20 is provided within a cylindrical support tube 21 fixed to the frame 12 of the light source apparatus 10. The support tube 21 contains a cylindrical, light condensing tube 23 that is open at an end on the side facing the lamp 11 and which has its longitudinal axis aligned with the optical axis of the illuminating light radiated from the lamp 11. A condenser lens 22 is fixed to the open end of the light condensing tube 23.

The light condensing tube 23 is fitted within the support tube 21 such that it is slidable along the longitudinal axis. The support tube 21 is loaded with a compressive coil spring 24 that urges the light condensing tube 23 in a forward direction (to come closer to the lightguide connector 3).

A key slot 25 is formed in an inner peripheral surface of the support tube 21, and a pin 26 is erected from the outer peripheral surface of the light condensing tube 23. The pin 26 is in engagement with the key slot 25 to ensure that the light condensing tube 23 will not rotate relative to the support tube 21.

A connector receptacle 27 is formed at the center of the front end wall of the light condensing tube 23 as a tapered hole that progressively decreases in diameter in a direction toward the lamp 11. The tip portion of the lightguide connector 3 is formed as a tapered rod that just fits into the connector receptacle 27.

The illuminating light emitted from the lamp 11 is allowed to converge with the condenser lens 22 so that it is focused near the connector receptacle 27. Since the greater part of the illumination from the lamp 11 consists of rays of parallel light, it is always focused near the connector receptacle 27 notwithstanding axial movements of the light condensing tube 23.

The lightguide fiber bundle 4 is passed through the lightguide connector 3 such that its entrance end face 4a is flush with the tip surface of the lightguide connector 3.

The lightguide connector 3 is inserted into the support tube 21 through a guide hole 28 penetrated through the front end wall of the support tube 21 along the longitudinal axis thereof. The inserted lightguide connector 3 has its tapered end fitted into the connector receptacle 27. As a result, the entrance end face 4a of the lightguide fiber bundle 4 is situated near the position in which the rays of illuminating light converge, whereupon the illuminating light is entered into the lightguide fiber bundle 4.

The engagement between the lightguide connector 3 and the connector receptacle 27 compresses the coil spring 24 to absorb any dimensional errors and other factors that may potentially cause rattling. Indicated by 29 is a ventilation window through which air is passed to cool the mechanism around the light condensing portion.

The filter inserting and retracting mechanism 30 is provided between the illuminating light converging mechanism 20 and the light source lamp 11, and adapted to be such that a filter frame 32 fitted with a light attenuating filter 31 and movable in directions (as indicated by two-headed arrow A) perpendicular to the optical axis of the illuminating light is driven in association with the axial movements of the light condensing tube 23.

Figure 2:
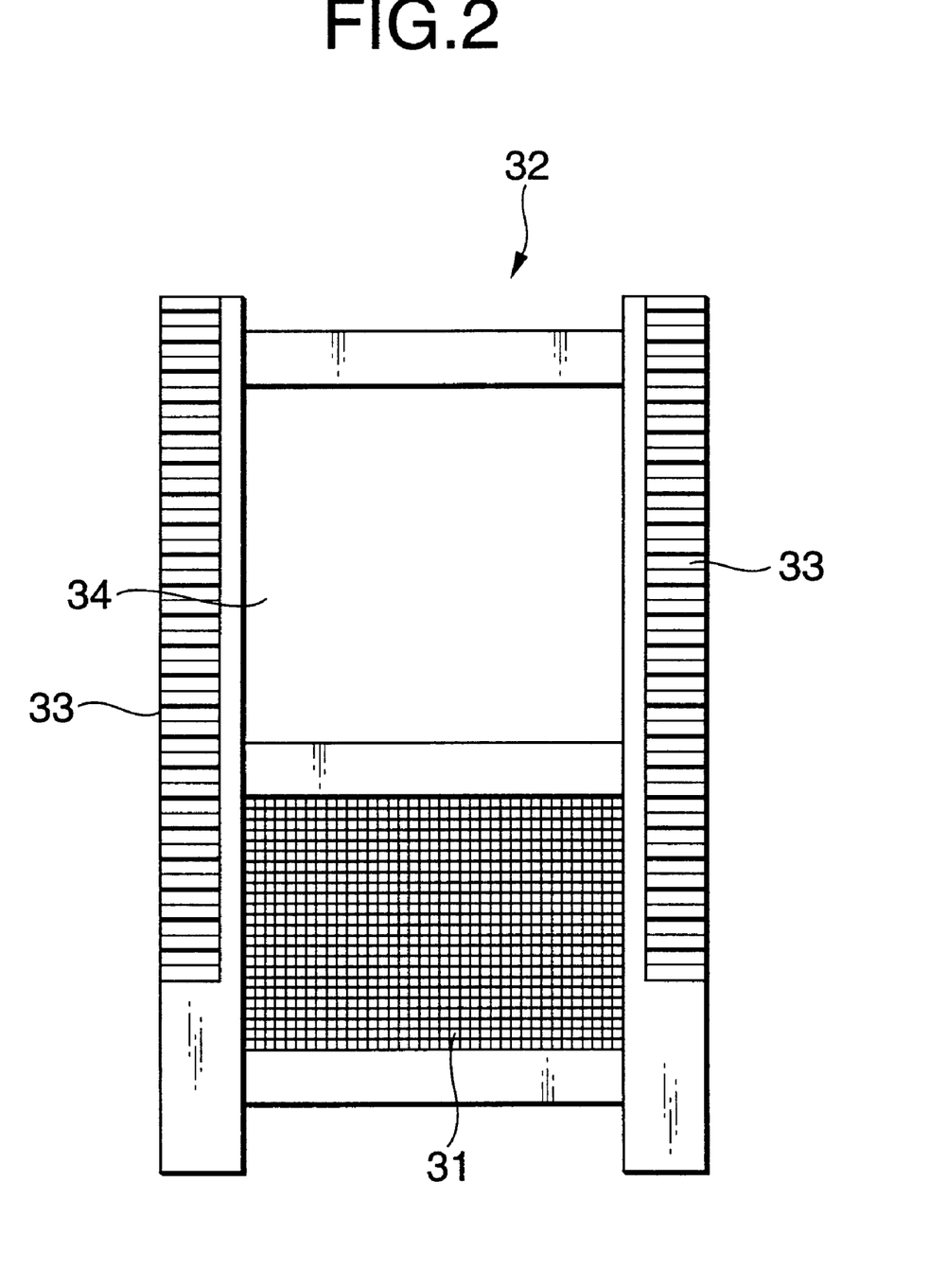
FIG. 2 is a front view of a filter frame used in the embodiment of the invention.

As shown in FIG. 2, the filter frame 32 has a pair of spaced, straight, parallel racks 33, with half of the space between the racks being fitted with the light attenuating filter 31 in the form of a metal screen whereas the other half of the space being left open as indicated by 34.

Figure 3:
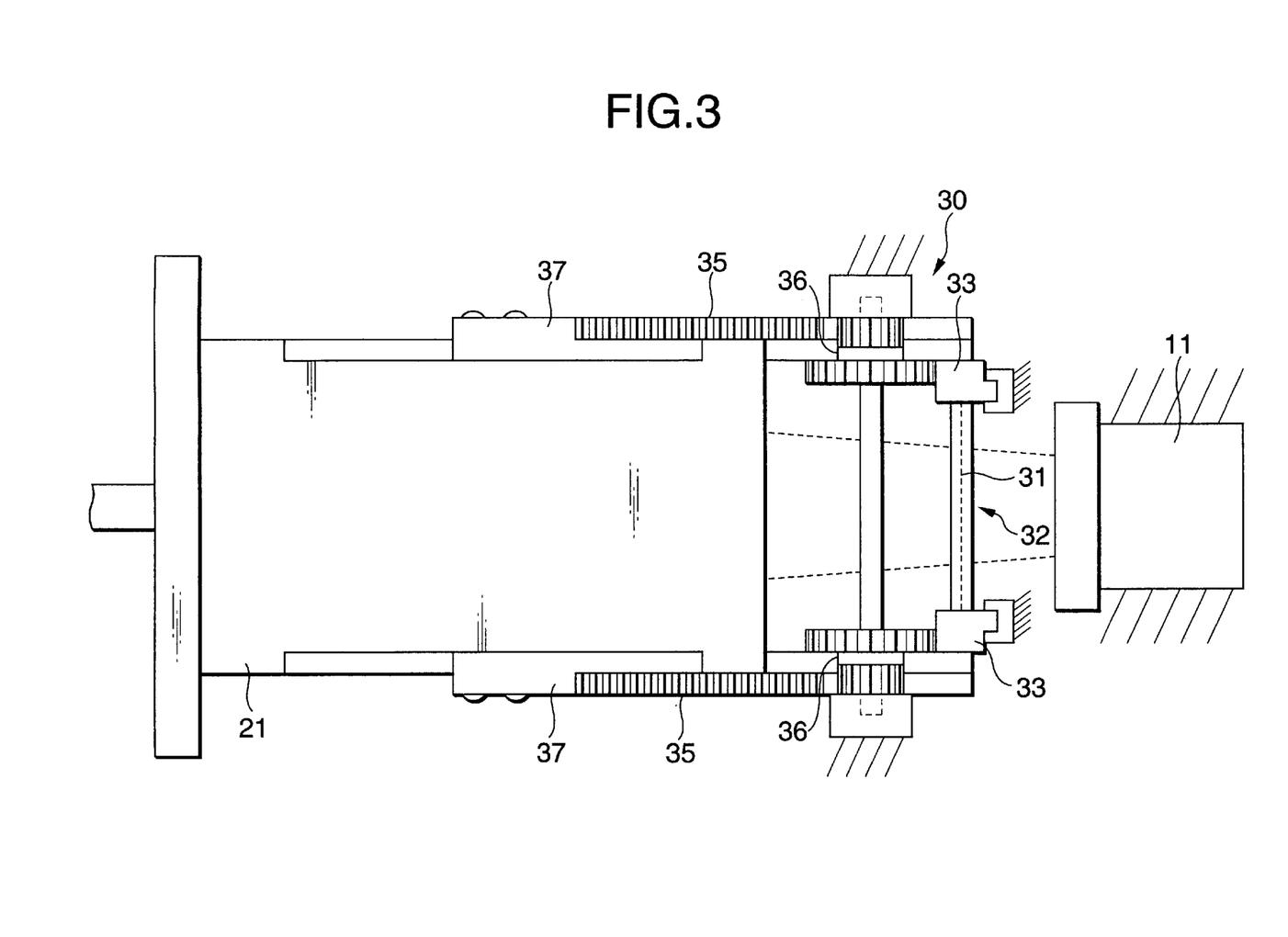
FIG. 3 is a plan view of a filter inserting and retracting mechanism used in the embodiment of the invention.

As also shown by a plan view in FIG. 3, a pair of arms 37 are coupled to the right and left sides of the light condensing tube 23 to extend rearwardly, and racks 35 are formed on the respective arms. Each rack 35 meshes with the small-diameter wheel of a double gear 36 whereas the large-diameter wheel meshes with the corresponding rack 33 on the filter frame 32.

Given this arrangement, if the light condensing tube 23 moves along its longitudinal axis (parallel to the optical axis of the illuminating light), the filter frame 32 is driven in a direction perpendicular to the optical axis and, as shown in FIG. 1 for the case where the short lightguide connector 3 in a new system is connected to the light source apparatus 10, the light attenuating filter 31 is retracted from the optical path of the illuminating light.

Figure 4:
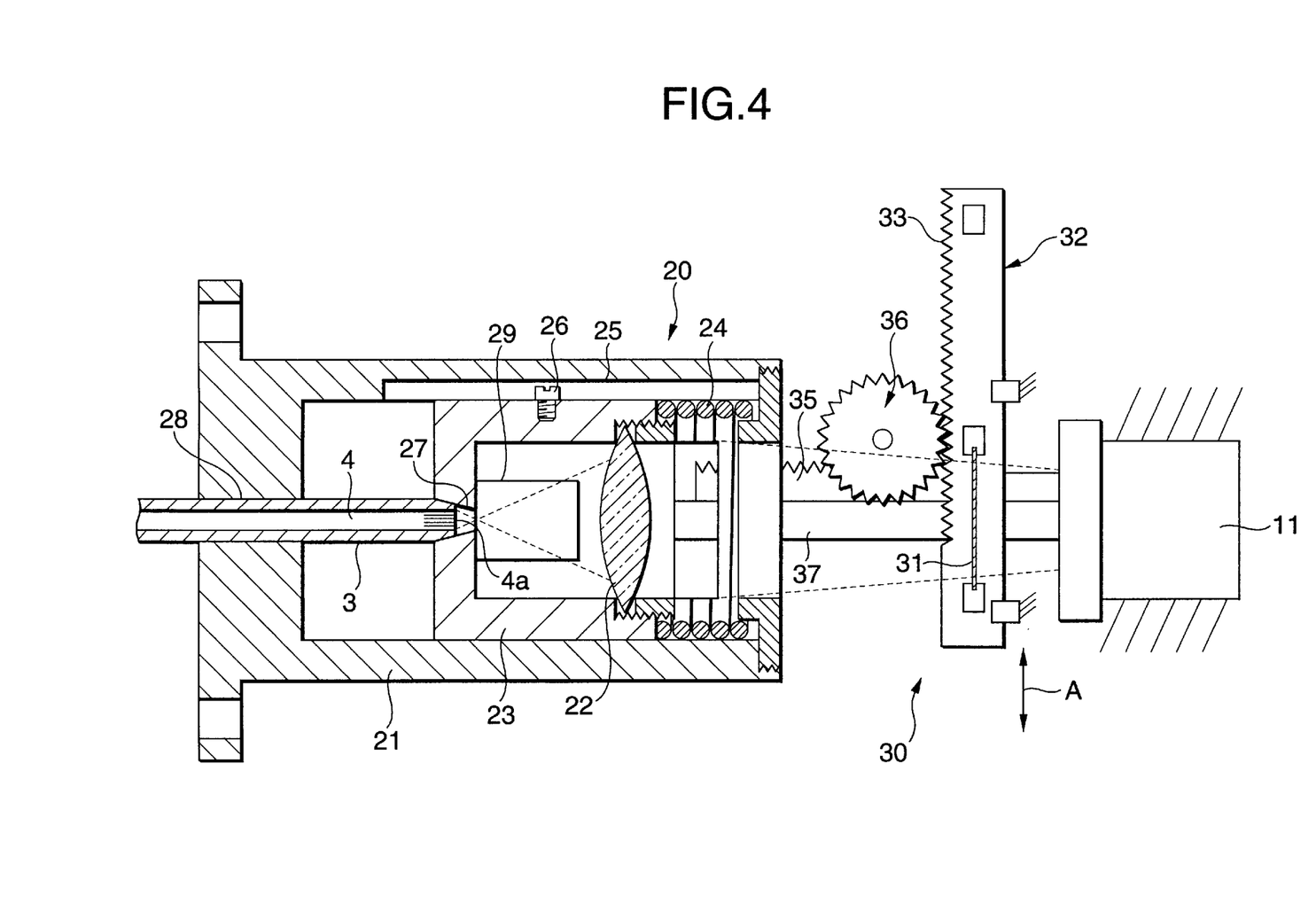
FIG. 4 is a longitudinal section of the embodiment of the invention in which a long lightguide connector is connected to a light source apparatus.

FIG. 4 shows the case where a long lightguide connector 3 in the old system is connected to the light source apparatus 10. As illustrated, the lightguide connector 3 being connected pushes the light condensing tube 23 toward the other end of the support tube 21 as it compresses the coil spring 24.

As a result, the filter frame 32 is driven to cause the light attenuating filter 31 to be inserted into the optical path of the illuminating light between the lamp 11 and the condenser lens 22. Even in this case, the rays of illuminating light are allowed to converge with the condenser lens 22 so that they are focused near the connector receptacle 27, in the neighborhood of which the entrance end face 4a of the lightguide fiber bundle 4 is located.

Thus, the light attenuating filter 31 retracts from the optical path of illuminating light when the short lightguide connector 3 for the new system is connected to the light source apparatus 10 whereas the same filter is automatically inserted into the optical path of the illuminating light when the long lightguide connector 3 for the old system is connected to the light source apparatus 10.

Figure 6:
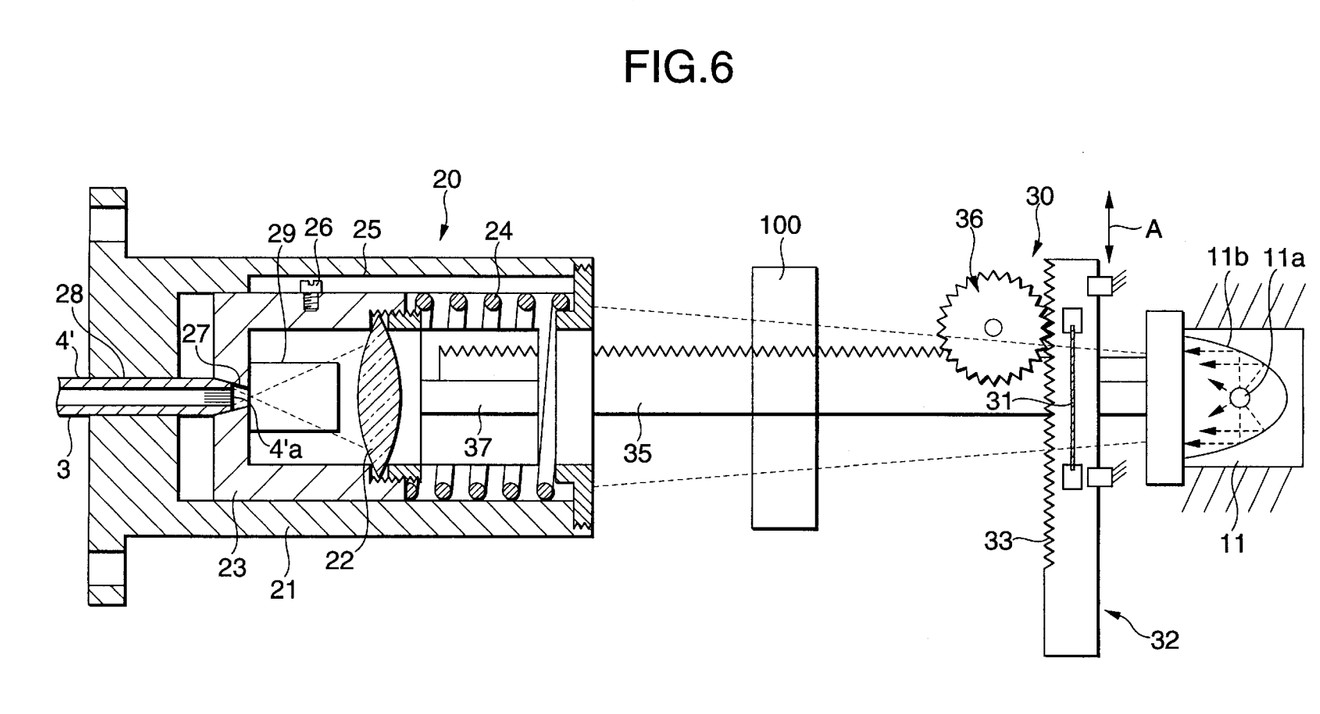
FIG. 6 is a longitudinal section of another embodiment of the invention in which a short lightguide connector is connected to a light source apparatus.

FIG. 6 shows a second embodiment of the present invention. In FIG. 6, components the same as or functionally equivalent to those shown in FIG. 1 to 5 are denoted by the same or similar reference numerals, so that the detailed description therefor is omitted here. The light source apparatus according to the second embodiment is designed so that the light attenuating filter 31 is inserted into the optical path of illuminating light when the short lightguide connector 3 is connected to the light source apparatus 10 whereas the same filter automatically retracts from the optical path of the illuminating light when the long lightguide connector 3 is connected to the light source apparatus 10. This can be simply achieved by changing the position of the light attenuating filter 31 on the filter frame 32 of the first embodiment. In addition, reference numeral 4' designates a lightguide fiber bundle made of resin (i.e. a bundle of plastic fibers), and reference numeral 100 designates a rotary filter or a diaphragm mechanism located between the entrance end face 4a of the lightguide fiber bundle 4 and the light source lamp 11.

Some new systems are available, which include a light source apparatus equipped with the rotary filter or the diaphragm mechanism that is to be disposed between the entrance end face 4a of the lightguide fiber bundle 4 and the light source lamp 11 when the endoscope is connected to the light source apparatus. The presence of the rotary filter or the diaphragm mechanism between the entrance end face 4a of the lightguide fiber bundle 4 and the light source lamp 11 ensures a relative long distance between the entrance end face 4a of the lightguide fiber bundle 4 and the light source lamp 11. Therefore, even in a case where the long lightguide connector 3 for the old system is connected to the light source apparatus 10, the lightguide connector 3 for the old system is free from the heat problem without the use of the light attenuating filter 31. However, in a case where the short light guide connector 3 supporting the lightguide plastic fiber bundle 4' therein for the new system is connected to the light source apparatus 10, the lightguide plastic fiber bundle 4' needs to be protected from heat, and thus the light attenuating filter 31 is automatically inserted into the optical path of illuminating light between the entrance end face 4'a of the lightguide fiber bundle 4' and the light source lamp 11.

What is claimed is:

1. An endoscopic light source apparatus in which an illuminating light entrance end face of an endoscope's lightguide connector is connected near a converging position at which rays of illuminating light emitted from a light source are allowed to converge with a condenser lens, said apparatus comprising:

an illuminating light converging mechanism in which said lightguide connector moves said condenser lens in a direction parallel to an optical axis of the illuminating light rays so that regardless of the length of said lightguide connector, the illuminating light entrance end face of said lightguide connector is located near the converging position of said rays of illuminating light; and a filter inserting and retracting mechanism which moves in operative association with said illuminating light converging mechanism such that a light attenuating filter is inserted into or retracted from said rays of illuminating light depending upon the length of said light guide connector.

2. The endoscopic light source apparatus according to claim 1, wherein said filter inserting and retracting mechanism is driven by said illuminating light converging mechanism in conjunction with the movement of the condenser lens of said illuminating light converging mechanism along the optical axis of the illuminating light rays.

3. The endoscopic light source apparatus according to claim 1, wherein said filter inserting and retracting mechanism allows said light attenuating filter to be inserted or retracted in a direction normal to said optical axis of the illuminating light.

4. The endoscopic light source apparatus according to claim 1, wherein said light attenuating filter is inserted into said rays of illuminating light when said light guide connector is long but said light attenuating filter is not inserted into said rays of illuminating light when said lightguide connector is short.

5. The endoscopic light source apparatus according to claim 1, wherein said light attenuating filter is inserted into said rays of illuminating light when said lightguide connector is short, and said light attenuating filter is retracted from said rays of illuminating light when said light guide connector is long and a predetermined distance is provided between the illuminating lightguide entrance end face and the light source, the predetermined distance being a distance such that the lightguide connector avoids heat problems caused by the light source.

6. The endoscopic light source apparatus according to claim 5, wherein said long lightguide connector is made of glass fiber, and said short lightguide connector made of plastic fiber.

7. The endoscopic light source apparatus according to claim 1, wherein the light source emits rays of both parallel light and diffusing light.

8. An endoscopic light source apparatus to which a lightguide connector of an endoscope is connected, said apparatus comprising:
   a lamp;
   a light condensing tube movable toward and away from said lamp on and along an optical path of rays emitted from said lamp, said tube having a connector receptacle, and supporting a condenser lens at a fixed distance from said connector receptacle, said connector receptacle being arranged opposite from said lamp with respect to said condenser lens on and along said optical path; and
   a movable filter frame arranged between said condenser lens and said lamp, and kinematically coupled to said light condensing tube, said filter frame supporting a light attenuating filter.

9. An endoscopic light source apparatus to which a long lightguide connector and a short lightguide connector is connectable, a distance between an illuminating light entrance end face and a light source being different when the long lightguide connector is connected than when the short lightguide connector is connected, the endoscopic light source apparatus comprising:
   a condenser lens that converges rays of illuminating light emitted from the light source;
   an illuminating light converging mechanism that, upon connection of one of the long and short light guide connectors, moves the condenser lens in a direction parallel to an optical axis of the rays of illuminating light so that the illuminating light entrance end face is located near a converging position of the rays of illuminating light, regardless of a difference in the distance between the illuminating light entrance end face and the light source due to the length of the connected one of the long and short lightguide connectors;
   a light attenuating filter;
   a filter inserting and retracting mechanism that moves the light attenuating filter in association with the movement of the condenser lens such that the light attenuating filter is inserted into or retracted from the rays of illuminating light depending upon the length of the connected one of the long and short lightguide connectors.

* * * * *